US012723236B2

(12) United States Patent
Hiraoka et al.

(10) Patent No.: US 12,723,236 B2
(45) Date of Patent: Sep. 1, 2026

(54) METHOD FOR PRODUCING CELL AGGREGATE

(71) Applicants: TOPPAN Holdings Inc., Tokyo (JP); OSAKA UNIVERSITY, Suita (JP)

(72) Inventors: Yasuyuki Hiraoka, Tokyo (JP); Michiya Matsusaki, Suita (JP)

(73) Assignees: TOPPAN HOLDINGS INC., Tokyo (JP); OSAKA UNIVERSITY, Osaka (JP)

( * ) Notice: Subject to any disclaimer, the term of this patent is extended or adjusted under 35 U.S.C. 154(b) by 420 days.

(21) Appl. No.: 18/552,007

(22) PCT Filed: Mar. 2, 2022

(86) PCT No.: PCT/JP2022/008909
§ 371 (c)(1),
(2) Date: Sep. 22, 2023

(87) PCT Pub. No.: WO2022/209552
PCT Pub. Date: Oct. 6, 2022

(65) Prior Publication Data

US 2024/0191202 A1 Jun. 13, 2024

(30) Foreign Application Priority Data

Apr. 1, 2021 (JP) ................................ 2021-062955

(51) Int. Cl.
*C12N 5/071* (2010.01)

(52) U.S. Cl.
CPC ........ *C12N 5/0671* (2013.01); *C12N 2501/91* (2013.01); *C12N 2513/00* (2013.01); *C12N 2533/54* (2013.01); *C12N 2533/56* (2013.01)

(58) Field of Classification Search
CPC .............. C12N 5/0671; C12N 2501/91; C12N 2513/00; C12N 2533/54; C12N 2533/56; C12N 5/067
See application file for complete search history.

(56) References Cited

FOREIGN PATENT DOCUMENTS

| | | | | |
|---|---|---|---|---|
| EP | 3421588 A1 * | 1/2019 | .......... C12N 5/0656 |
| JP | 2012-115254 | 6/2012 | |
| JP | 2019-502382 | 1/2019 | |
| JP | 2019-033732 | 3/2019 | |
| JP | 2019033732 A * | 3/2019 | |
| WO | WO 2017/117333 A1 | 7/2017 | |
| WO | WO 2017/146124 A1 | 8/2017 | |
| WO | WO 2018/143286 A1 | 8/2018 | |

OTHER PUBLICATIONS

Buyl, K et al., 2014. Measurement of albumin secretion as functionality test in primary hepatocyte cultures. In Protocols in In Vitro Hepatocyte Research (pp. 303-308). New York, NY: Springer New York. (Year: 2014).*
English Translation of IPRP (PCT/IB/338 and PCT/IB/373) (Oct. 12, 2023 and Oct. 3, 2023) and the Written Opinion of ISA (PCT/ISA/237) issued in counterpart International Application No. PCT/JP2022/008909 dated May 24, 2022 (6 pages).
International Search Report issued in International Application PCT/JP2022/008909 dated May 24, 2022.

* cited by examiner

*Primary Examiner* — Christopher M Babic
*Assistant Examiner* — Masudur Rahman
(74) *Attorney, Agent, or Firm* — XSENSUS LLP

(57) ABSTRACT

Disclosed is a method for producing a cell aggregate having bile canaliculi, including a contact step of bringing cells including hepatocytes into contact with heparin in an aqueous medium and a culture step of culturing the cells brought in contact with the heparin to form the cell aggregate. A concentration of heparin in the aqueous medium when it is brought into contact with the cells may be 0.5 mg/mL or more.

8 Claims, 9 Drawing Sheets

*Fig.2*

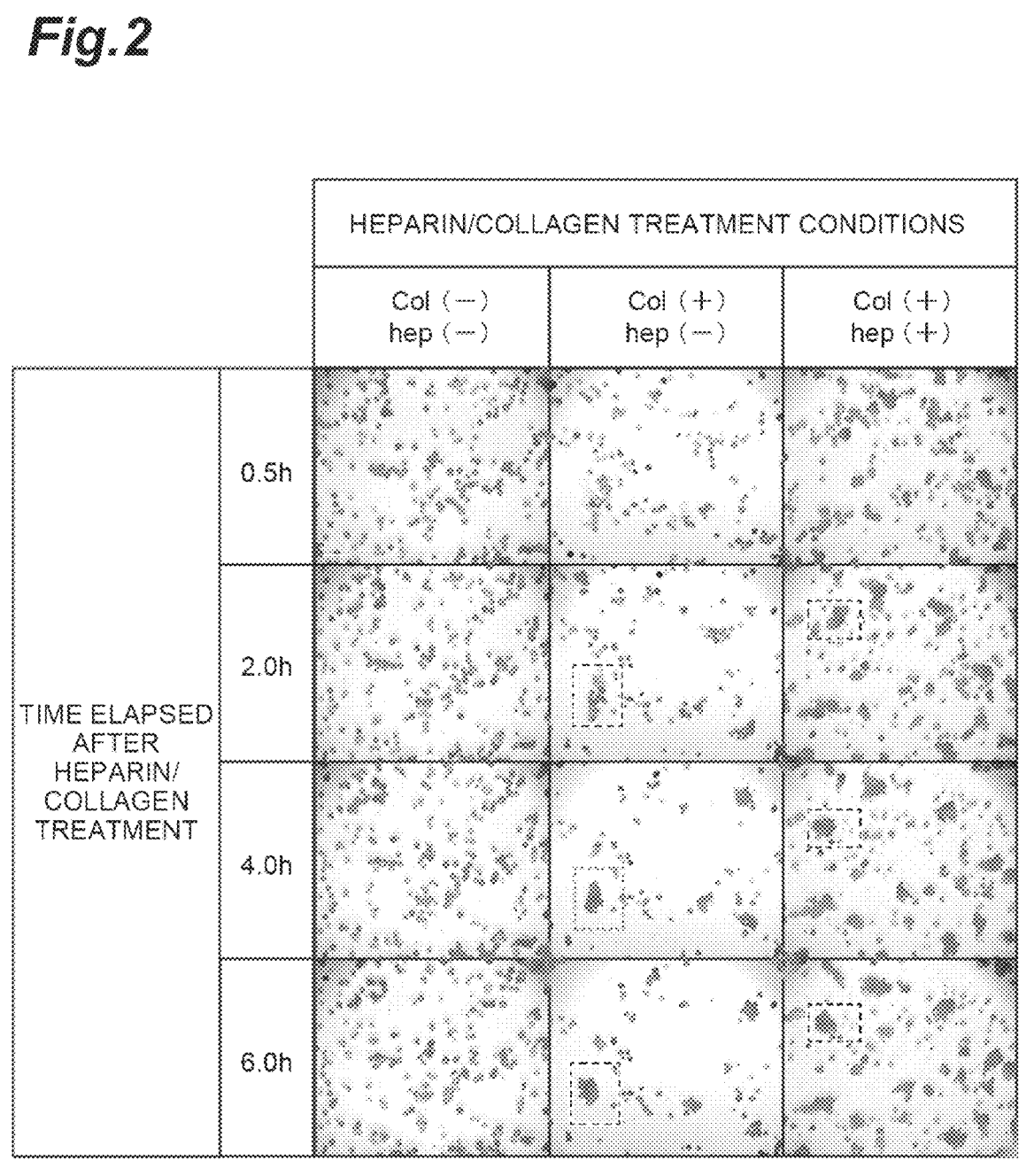

| | | HEPARIN/COLLAGEN TREATMENT CONDITIONS | | |
|---|---|---|---|---|
| | | Col (−) hep (−) | Col (+) hep (−) | Col (+) hep (+) |
| TIME ELAPSED AFTER HEPARIN/ COLLAGEN TREATMENT | 0.5h | | | |
| | 2.0h | | | |
| | 4.0h | | | |
| | 6.0h | | | |

*Fig.3*

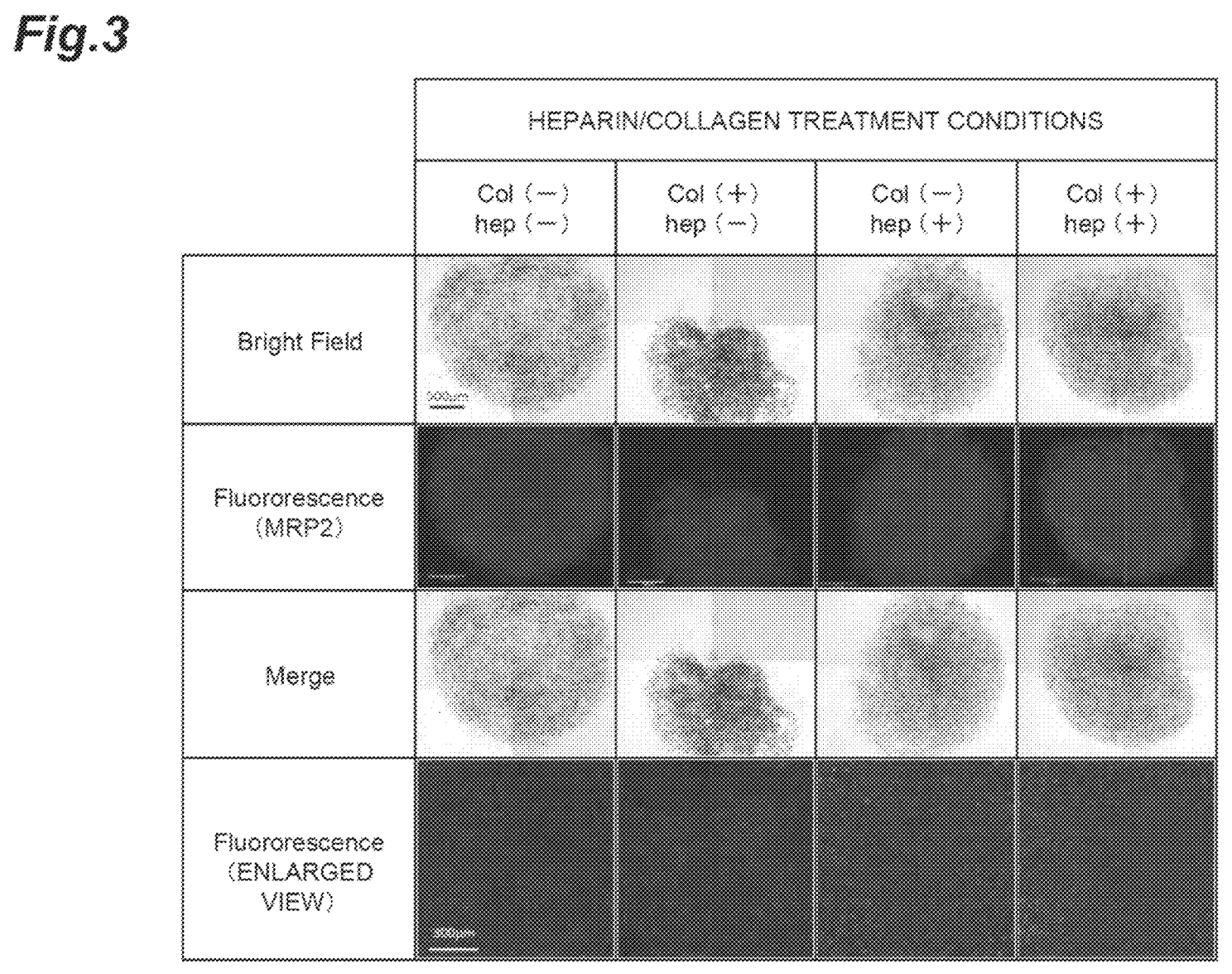

HEPARIN/COLLAGEN TREATMENT CONDITIONS

Col (−) hep (−)

Col (+) hep (−)

Col (−) hep (+)

Col (+) hep (+)

Bright Field

Fluororescence (MRP2)

Merge

Fluororescence (ENLARGED VIEW)

Fig.4

| | HEPARIN/COLLAGEN TREATMENT CONDITIONS | | | |
|---|---|---|---|---|
| | Col (−) hep (−) | Col (+) hep (−) | Col (−) hep (+) | Col (+) hep (+) |
| TRIAL 1 | | | | |
| TRIAL 2 | | | | |
| TRIAL 3 | | | | |

Fig.5
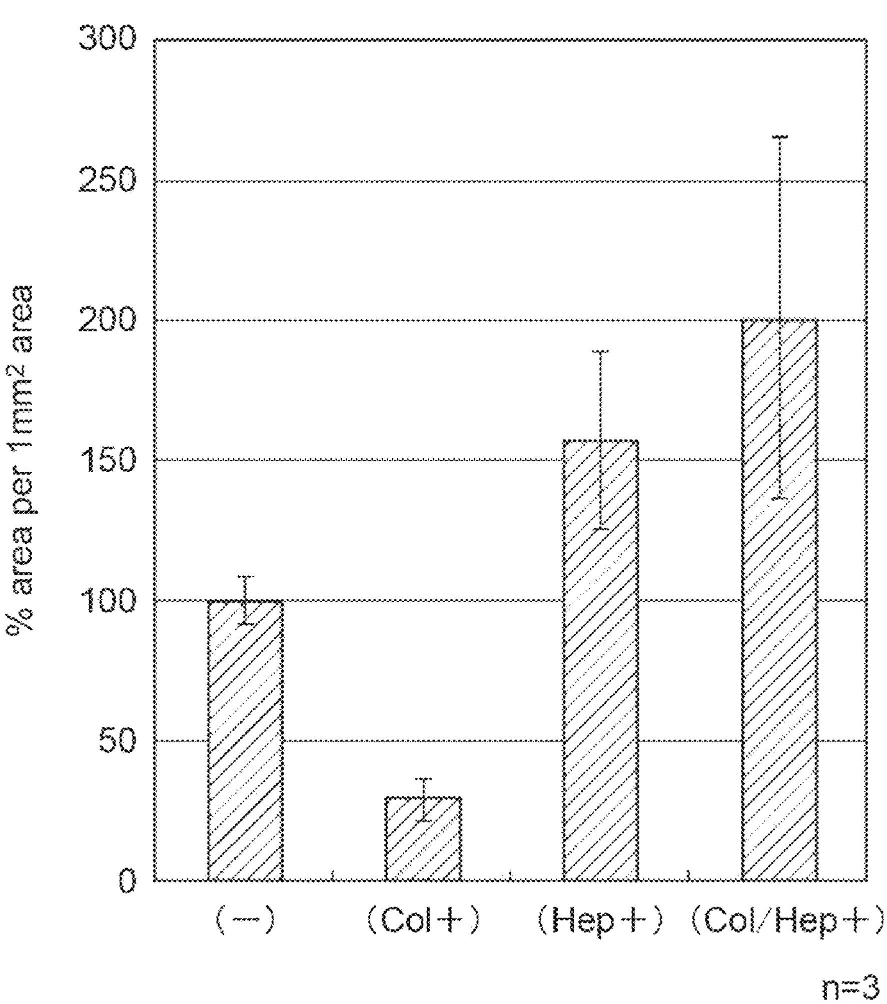
EXPRESSION AREA PERCENTAGE
OF MRP2 PER AREA
% area per 1mm² area
300
250
200
150
100
50
0
(−)
(Col+)
(Hep+)
(Col/Hep+)
n=3

(a)

(b)

(c)

(a)

(b)

(c)

(a)

(b)

(c)

(a)
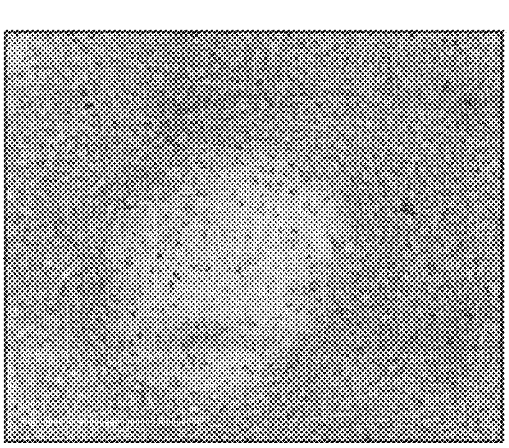
(b)
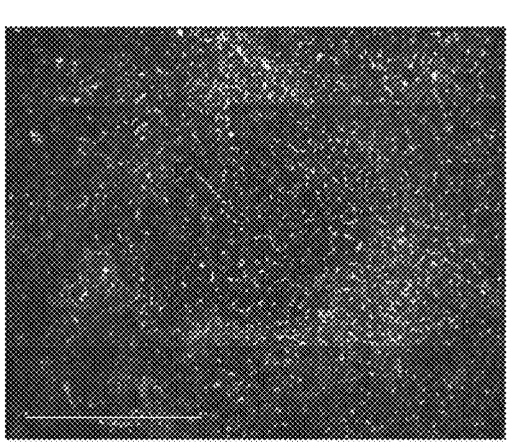
(c)
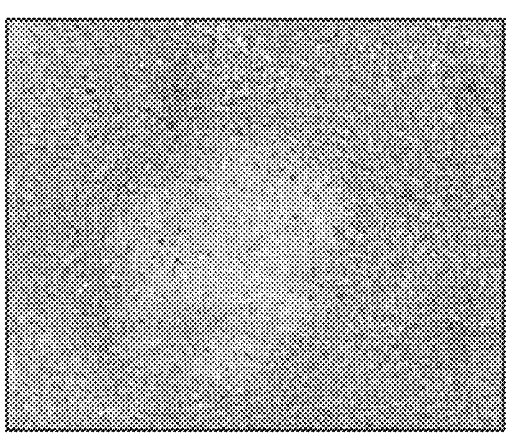

METHOD FOR PRODUCING CELL AGGREGATE

CROSS REFERENCE TO RELATED APPLICATIONS

This application is a 35 USC 371 U.S. national stage application of International Application No. PCT/JP2022/008909, filed on Mar. 2, 2022, which claims the priority benefit to Japanese Application No. 2021-062955, filed on Apr. 1, 2021. The International Application and the Japanese Application are incorporated by reference herein in their entirety.

TECHNICAL FIELD

The present invention relates to a method for producing a cell aggregate.

BACKGROUND ART

The liver is an organ with a high likelihood of toxicity being manifested therein in the process of drug development, and Drug-Induced-Liver-Injury (DILI) caused by ingestion of pharmaceutical products is a main cause of discontinuation of development and sales of pharmaceutical products. Compounds that can cause DILI (hereinafter referred to as DILI compounds) are not always easy to identify in animal experiments, and if this disorder is discovered after clinical tests or pharmaceutical product sales, since a large loss occurs, an evaluation system that can predict DILI compounds in advance is required. A structure that artificially simulates a living tissue is beneficial for an evaluation system that can predict DILI compounds in advance.

As a method for producing a structure that artificially stimulates a living tissue, for example, a method for producing a three-dimensional tissue by culturing covered cells in which the entire surface of cultured cells is covered with an adhesive membrane (Patent Literature 1), a method for producing a three-dimensional cell tissue including mixing cells with a cationic substance and an extracellular matrix component to obtain a mixture, collecting cells from the obtained mixture, and forming a cell aggregate on a substrate (Patent Literature 2) and the like are known. In addition, the inventors proposed a method for producing a three-dimensional tissue with a high collagen concentration by bringing cells into contact with endogenous collagen, and preferably additionally bringing into contact with fibrous exogenous collagen (Patent Literature 3).

CITATION LIST

Patent Literature

[Patent Literature 1] Japanese Unexamined Patent Publication No. 2012-115254

[Patent Literature 2] PCT International Publication No. WO2017/146124

[Patent Literature 3] PCT International Publication No. WO2018/143286

SUMMARY OF INVENTION

Technical Problem

An object of the present invention is to provide a method for producing a cell aggregate that can be used as a liver model that is closer to the in vivo state.

Solution to Problem

That is, the present invention relates to, for example, the following inventions.

[1] A method for producing a cell aggregate having bile canaliculi, including:
a contact step of bringing cells including hepatocytes into contact with heparin in an aqueous medium; and
a culture step of culturing the cells brought in contact with the heparin to form the cell aggregate.

[2] The method according to [1],
wherein the hepatocytes are mature hepatocytes.

[3] The method according to [1] or [2],
wherein the concentration of heparin when it is brought into contact with the cells in the aqueous medium is 0.5 mg/mL or more.

[4] The method according to any one of [1] to [3],
wherein the proportion of the number of hepatocytes in the total number of cells is 65% or more.

[5] The method according to any one of [1] to [4],
wherein, in the contact step, the cells are additionally brought into contact with extracellular matrix components.

[6] The method according to [5],
wherein the extracellular matrix components are collagen components.

[7] The method according to any one of [1] to [6],
wherein the expression intensity percentage of MRP2 represented by the following Formula (1) is 120% or more, expression intensity percentage of MRP2=X/Y×100 (1)
wherein in Formula (1),
X represents an expression intensity of MRP2 in the cell aggregate formed in the culture step, and
Y represents an expression intensity of a control cell aggregate formed by culturing cells including hepatocytes without contact with heparin and extracellular matrix components.

Advantageous Effects of Invention

According to the present invention, it is possible to provide a method for producing a cell aggregate that can be used as a liver model that is closer to the in vivo state.

BRIEF DESCRIPTION OF DRAWINGS

FIG. 2 shows microscope images of the observation results of aggregation tendencies of cells treated with collagen (col) and heparin (hep).

FIG. 3 shows microscope images of the MRP2 expression state of cell aggregates after 3 days of culture.

FIG. 4 shows microscope images of the observation results MRP2 expression of cell aggregates after 3 days of culture.

FIG. 5 is a graph showing the image analysis results of the expression intensity percentage of MRP2.

FIG. 9 shows microscope images of the bile acid assay results, FIG. 9(*a*) shows a bright field, FIG. 9(*b*) shows fluorescence, and FIG. 9(*c*) is an image of (a) and (b) merged.

DESCRIPTION OF EMBODIMENTS

Figure 1:
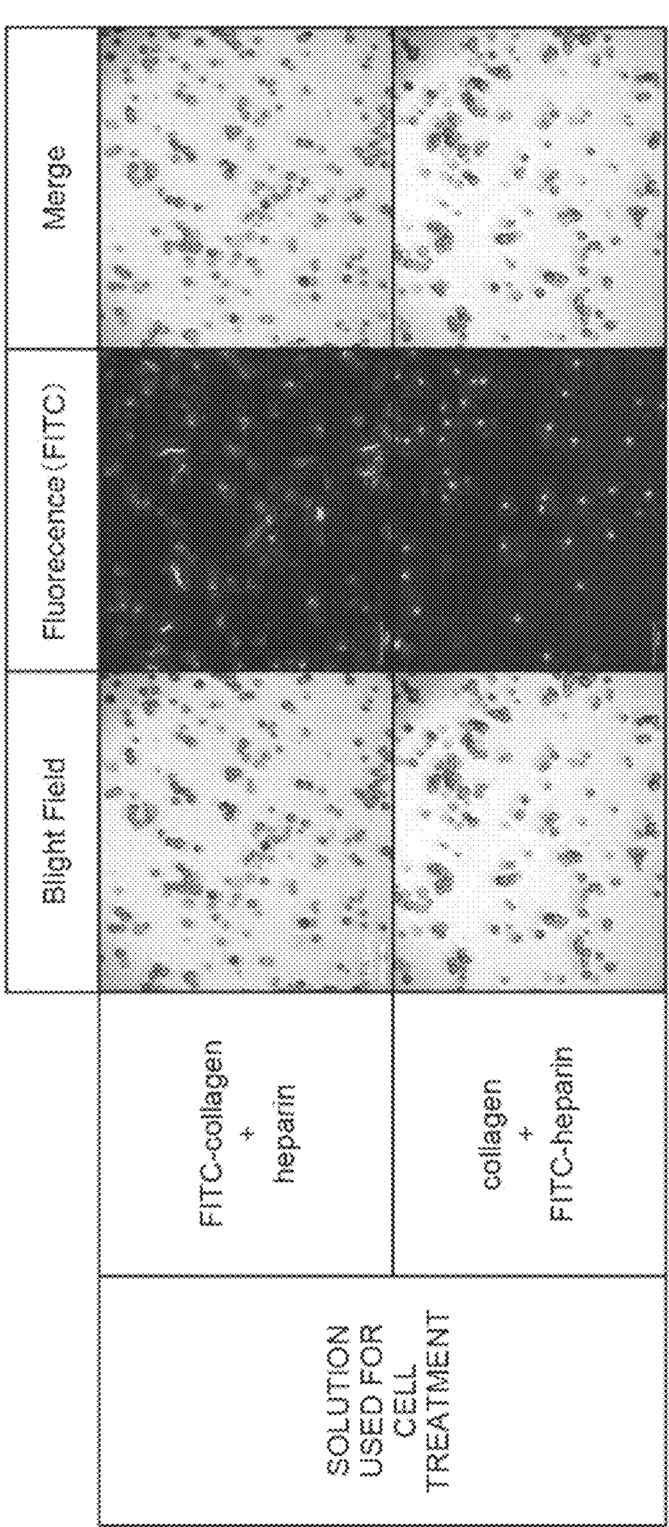
FIG. 1 shows microscope images of the observation results of collagen and heparin deposited in cells.

Hereinafter, forms for implementing the present invention will be described in detail. However, the present invention is not limited to the following embodiments.

[Cell Aggregate]

A method according to the present embodiment is a method for producing a cell aggregate having bile canaliculi, including a contact step of bringing cells including hepatocytes into contact with heparin in an aqueous medium, and a culture step of culturing the cells brought in contact with the heparin to form the cell aggregate.

The cell aggregate obtained by the method according to the present embodiment can be used as a liver model (hepatoid tissue), which is a living tissue model having functions similar to at least some functions of the liver and/or having a structure similar to at least a part of a structure of the liver.

In this specification, the "cell aggregate" is a cell aggregate (mass-like cell population) and is an aggregate artificially produced by cell culture. The cell aggregate may be a structure in which cells are three-dimensionally disposed (three-dimensional tissue) or a structure in which cells are two-dimensionally disposed.

The shape of the cell aggregate is not particularly limited, and examples thereof include a sheet shape, a spherical shape, substantially a spherical shape, an ellipsoidal shape, substantially an ellipsoidal shape, a hemispherical shape, substantially a hemispherical shape, a semicircular shape, substantially a semicircular shape, a rectangular parallelepiped shape, and substantially a rectangular parallelepiped shape. Here, the living tissue includes sweat glands, lymphatic vessels, sebaceous glands and the like, and has a more complex configuration than the cell aggregate. Therefore, the cell aggregate and the living tissue can be easily distinguished. In addition, the cell aggregate may be aggregated in a mass in which the cell aggregate is adhered to a support or aggregated in a mass in which the cell aggregate is not adhered to a support.

(Cells)

The cells may be somatic cells or germ cells. In addition, the cells may be stem cells, or may be cultured cells such as primary cultured cells, sub-cultured cells and cell line cells. In this specification, the "stem cells" are cells having a self-replication ability and pluripotency. Stem cells include pluripotent stem cells having an ability to differentiate into any cell tumor and tissue stem cells (also called somatic stem cells) having an ability to differentiate into specific cell tumors. Examples of pluripotent stem cells include embryonic stem cells (ES cells), somatic cell-derived ES cells (ntES cells) and induced pluripotent stem cells (iPS cells). Examples of tissue stem cells include mesenchymal stem cells (for example, bone marrow-derived stem cells), hematopoietic stem cells and neural stem cells.

Cells in the cell aggregate according to the present embodiment include hepatocytes. Hepatocytes are also referred to as hepatic parenchymal cells, and are, for example, cells having functions such as bile secretion and plasma protein secretion. Hepatocytes may be mature hepatocytes or other hepatocytes. The mature hepatocytes may be, for example, primary hepatocytes collected from the liver of an animal, cells obtained by culturing primary hepatocytes, or cultured cell lines in which primary hepatocytes are established. The other hepatocytes may be, for example, hepatoblasts artificially differentiated from stem cells. Examples of primary hepatocytes include primary human hepatocytes such as PXB Cell. Examples of cultured cell lines include cell lines derived from inactivated liver cancer cells such as HepG2. Examples of stem cells that differentiate into hepatoblasts include embryonic stem cells (ES cells), induced pluripotent stem cells (iPS cells), and mesenchymal stem cells. The hepatocytes contained in the cell aggregate according to the present embodiment are preferably non-cancerous cells such as primary hepatocytes and hepatoblasts. The hepatocytes may be mature hepatocytes and more preferably PXB Cell in consideration of ease of handling.

The hepatocytes contained in the cell aggregate may be of one type or two or more types. For example, the cell aggregate may contain a plurality of hepatocytes having different genotypes for proteins involved in liver functions. In addition, conversely, all hepatocytes contained in the cell aggregate may have the same genotype for proteins involved in liver functions. Examples of proteins involved in liver functions include drug-metabolizing enzymes.

The total number of cells constituting the cell aggregate according to the present embodiment is not particularly limited, and is appropriately determined in consideration of the thickness and shape of the cell aggregate to be constructed, the size of the cell culture container used for construction, and the like.

The proportion of the number of hepatocytes in the total number of cells in the cell aggregate (the number of hepatocytes/the total number of cells×100) may be 5% or more, 10% or more, 15% or more, 20% or more, 25% or more, 30% or more, 35% or more, 40% or more, 45% or more, 50% or more, 55% or more, 60% or more, or 65% or more, and may be 95% or less, 90% or less, 80% or less or 75% or less. The proportion of the number of hepatocytes in the total number of cells in the cell aggregate may be 60% or more and 80% or less, or 60% or more and 70% or less in order to enable a liver model that is closer to the in vivo state to be formed.

The cells may further include vascular endothelial cells in order to enable a liver model that is closer to the in vivo state to be formed. Vascular endothelial cells are squamous cells constituting the surface of the intravascular lumen. Vascular endothelial cells may be, for example, sinusoidal endothelial cells, or human umbilical vein-derived vascular endothelial cells (HUVEC). The sinusoidal endothelial cells are hepatic non-parenchymal cells (cells other than hepatocytes among cells constituting the liver), and are cells which have a large number of small pore aggregates (cribriform plate structure) in the cytoplasm and have a characteristic morphology different from other vascular endothelial cells such as lacking of a basement membrane. The vascular endothelial cells constituting the cell aggregate may be primary cells (primary vascular endothelial cells) collected from the liver of an animal (for example, human), cells in which primary cells are cultured, cultured cell lines in which primary cells are established, or cells artificially differentiated from stem cells. Examples of primary vascular endothelial cells include primary sinusoidal endothelial cells such as product model name 5000 (commercially available from ScienceIl). Examples of cultured cell lines include cultured cell lines such as product model name T0056 (commercially available from Applied Biological Materials). Examples of differentiated stem cells include embryonic stem cells (ES cells) and induced pluripotent stem cells (iPS cells). The vascular endothelial cells contained in the cell aggregate according to the present embodiment may be non-cancerous cells.

The proportion of the number of vascular endothelial cells in the total number of cells in cell aggregates (the number of vascular endothelial cells/the total number of cells×100) may be 5% or more, 10% or more, 15% or more, 20% or more, or 25% or more, and may be 50% or less, 45% or less, 40% or less, 35% or less, 30% or less, or 25% or less. The proportion of the number of vascular endothelial cells in the total number of cells in cell aggregates may be 5% or more and 40% or less, 5% or more and 35% or less, 10% or more and 35% or less, or 10% or more and 30% or less in order to enable a liver model that is closer to the in vivo state to be formed. The proportion of sinusoidal endothelial cells in the total number of cells in the cell aggregate may be within the above range.

The cells in the cell aggregate according to the present embodiment may further include hepatic stellate cells in order to enable a liver model that is closer to the in vivo state to be formed. The hepatic stellate cells are hepatic non-parenchymal cells (cells other than hepatocytes among cells constituting the liver) and have a function of storing vitamin A, and are present in the space of Disse, which is an area between hepatocytes and the sinusoid in the liver. The hepatic stellate cells may be, for example, primary cells (primary hepatic stellate cells) collected from the liver of an animal (for example, a human), cells obtained by culturing primary cells, cultured cell lines in which primary cells are established, or cells artificially differentiated from stem cells. Examples of primary hepatic stellate cells include primary hepatic stellate cells such as model number 5300 (commercially available from ScienceII). Examples of cultured cell lines include cultured cell lines such as LX-2. Examples of differentiated stem cells include embryonic stem cells (ES cells), induced pluripotent stem cells (iPS cells), and mesenchymal stem cells. The hepatic stellate cells contained in the cell aggregate according to the present embodiment may be non-cancerous cells.

The proportion of the number of hepatic stellate cells in the total number of cells in the cell aggregate (the number of hepatic stellate cells/the total number of cells×100) may be 1% or more, 2% or more, 3% or more, 4% or more, or 5% or more, and may be 20% or less, 15% or less, 14% or less, 13% or less, 12% or less or 11% or less. The proportion of the number of hepatic stellate cells in the total number of cells in the cell aggregate may be 1% or more and 15% or less, or 3% or more and 12% or less in order to enable a liver model that is closer to the in vivo state to be formed.

In the present embodiment, the cells may include cells other than hepatocytes, vascular endothelial cells and hepatic stellate cells. The other cells may be, for example, matured somatic cells, or undifferentiated cells such as stem cells. Specific examples of somatic cells include for example, nerve cells, dendritic cells, immune cells, lymphatic endothelial cells, fibroblasts, epithelial cells (excluding hepatocytes), cardiomyocytes, pancreatic islet cells, smooth muscle cells, bone cells, alveolar epithelial cells, and spleen cells. Examples of stem cells include ES cells, iPS cells, and mesenchymal stem cells. The other cells may be normal cells or cells in which any cell function is enhanced or inhibited such as cancer cells. "Cancer cells" are cells derived from somatic cells and having an acquired infinite proliferative ability.

The origin of hepatocytes, vascular endothelial cells, and hepatic stellate cells contained in the cells or the other cells is not particularly limited, and for example, cells derived from mammals such as humans, monkeys, dogs, cats, rabbits, pigs, cows, mice, and rats may be used.

The cells in the cell aggregate according to the present embodiment may not include cells induced to differentiate from induced pluripotent stem cells (iPS cells). That is, the cells used in the contact step may be mature cells. When the cells in the cell aggregate according to the present embodiment do not include cells induced to differentiate from iPS cells, it is easier to determine a degree of differentiation from iPS cells, a proportion of differentiated cells in all cells, and the like, and as a result, it is easier to determine the content of each of the cells constituting the cell aggregate.

In the contact step, cells including hepatocytes are brought into contact with heparin in an aqueous medium. Examples of methods of bringing cells into contact with heparin include a method of suspending cells in a solution containing heparin, a method of adding heparin or a solution containing heparin to a cell-containing solution containing cells, and a method of adding heparin or a solution containing heparin and cells or a cell-containing solution containing cells to an aqueous medium prepared in advance. Heparin to be added may be in the form of a salt.

The concentration of heparin when it is brought into contact with cells in the aqueous medium based on the total amount of the aqueous medium may be 0.1 mg/mL or more, 0.2 mg/mL or more, 0.3 mg/mL or more, 0.4 mg/mL or more, or 0.5 mg/mL or more. The concentration of heparin when it is brought into contact with cells in the aqueous medium based on the total amount of the aqueous medium may be 12.0 mg/mL or less, 10.0 mg/mL or less, 8.0 mg/mL or less, 6.0 mg/mL or less, 5.0 mg/mL or less, 3.0 mg/mL or less, 1.0 mg/mL or less, 0.8 mg/mL or less, or 0.6 mg/mL or less. The concentration of heparin when it is brought into contact with cells in the aqueous medium based on the total amount of the aqueous medium may be 0.1 mg/mL or more and 12.0 mg/mL or less, 0.1 mg/mL or more and 10.0 mg/mL or less, 0.1 mg/mL or more and 8.0 mg/mL or less, 0.1 mg/mL or more and 6.0 mg/mL or less, 0.2 mg/mL or more and 12.0 mg/mL or less, 0.2 mg/mL or more and 10.0 mg/mL or less, 0.2 mg/mL or more and 8.0 mg/mL or less, 0.2 mg/mL or more and 6.0 mg/mL or less, 0.3 mg/mL or more and 12.0 mg/mL or less, 0.3 mg/mL or more and 10.0 mg/mL or less, 0.3 mg/mL or more and 8.0 mg/mL or less, 0.3 mg/mL or more and 6.0 mg/mL or less, 0.4 mg/mL or more and 12.0 mg/mL or less, 0.4 mg/mL or more and 10.0 mg/mL or less, 0.4 mg/mL or more and 8.0 mg/mL or less, 0.4 mg/mL or more and 6.0 mg/mL or less, 0.5 mg/mL or more and 12.0 mg/mL or less, 0.5 mg/mL or more and 10.0 mg/mL or less, 0.5 mg/mL or more and 8.0 mg/mL or less, or 0.5 mg/mL or more and 6.0 mg/mL or less. When the concentration of heparin when it is brought into contact with cells in the aqueous medium is within the above range, it is possible to form a liver model that is closer to a living body.

For example, the amount of heparin in the contact step may be 0.001 mg or more or 0.01 mg or more, and may be 1 mg or less or 0.1 mg or less with respect to 300,000 cells (the number of cells when they are brought into contact with heparin).

The origin of heparin is not particularly limited, and for example, cells derived from mammals such as humans, monkeys, dogs, cats, rabbits, pigs, cows, mice, and rats may be used.

The "aqueous medium" is a liquid medium containing water as an essential constituent component. The aqueous medium may be an aqueous medium containing a cationic substance. The aqueous medium containing a cationic substance may be, for example, a tris-hydrochloric acid buffer solution, a tris-maleate buffer solution, a bis-tris-buffer solution, or a cationic buffer solution such as HEPES(4-(2-hydroxyethyl)-1-piperazineethanesulfonic acid). The aqueous medium containing a cationic substance may be a medium containing a cationic compound such as ethanolamine, diethanolamine, triethanolamine, polyvinylamine, polyallylamine, polylysine, polyhistidine, polyarginine as a cationic substance and water. As the aqueous medium, a medium can be used. Examples of mediums include a liquid medium such as a Dulbecco's Modified Eagle medium (DMEM) and an endothelial cell growth medium (EGM2). The liquid medium may be a mixed medium in which two types of mediums are mixed.

The concentration and the pH of the cationic substance (for example, tris in a tris-hydrochloric acid buffer solution) in the aqueous medium containing a cationic substance are not particularly limited as long as it does not adversely affect cell growth and construction of the cell aggregate. For example, the concentration of the cationic substance based on the total amount of the aqueous medium containing a cationic substance may be 10 to 200 mM, 30 to 150 mM, or 50 to 120 mM. The pH of the aqueous medium (for example, cationic buffer solution) may be 6.0 to 8.0, 6.8 to 7.8, 6.8 to 7.6, or 7.2 to 7.6.

In the contact step, cells may be additionally brought into contact with an extracellular matrix component. When cells are additionally brought into contact with an extracellular matrix component, the cells are more likely to aggregate. In addition, when cells are additionally brought into contact with an extracellular matrix component, cell aggregates in which cells are three-dimensionally disposed are more likely to be formed. In addition, when cells are additionally brought into contact with an extracellular matrix component (particularly, when cells are brought into contact with a collagen component), the expression intensity percentage of MRP2 to be described below tends to be higher, and it is easier to obtain a liver model that is closer to the in vivo state. In addition, when cells are additionally brought into contact with an extracellular matrix component in the contact step, a thicker structure (three-dimensional structure) is likely to be obtained.

Examples of methods of additionally bringing cells into contact with an extracellular matrix component include a method of suspending cells in a solution containing an extracellular matrix component and heparin, a method of adding a solution containing an extracellular matrix component and heparin to a cell-containing solution containing cells, and a method of adding heparin or a solution containing heparin, cells or a cell-containing solution, and an extracellular matrix component or a solution containing an extracellular matrix component to an aqueous medium prepared in advance.

In this specification, the "extracellular matrix component" is an aggregate of extracellular matrix molecules formed by a plurality of extracellular matrix molecules. The extracellular matrix is a substance that is present outside cells in an organism. As the extracellular matrix, any substance can be used as long as it does not adversely affect cell growth and formation of cell aggregates. Specific examples include collagen, elastin, proteoglycan, fibronectin, hyaluronic acid, laminin, vitronectin, tenascin, entactin, fibrillin and cadherin, but the present invention is not limited thereto. The extracellular matrix components may be used alone or a combination thereof may be used. The extracellular matrix components may contain, for example, collagen components or may be collagen components. When the extracellular matrix component is a collagen component, it becomes easier to aggregate cells. When the extracellular matrix component is a collagen component, the collagen component functions as a scaffold for cell adhesion, and formation of a three-dimensional cell aggregate is further promoted. The extracellular matrix component in the present embodiment is preferably a substance present outside cells of an animal, that is, an extracellular matrix component of an animal. The extracellular matrix molecule may be a modifier or a variant of the above extracellular matrix molecule or may be a polypeptide such as a chemically synthesized peptide as long as it does not adversely affect cell growth and formation of cell aggregates.

The extracellular matrix components may have a repetition of a sequence represented by Gly-X-Y, which is a characteristic of collagen. Here, Gly represents a glycine residue, and X and Y each independently represent an arbitrary amino acid residue. The plurality of Gly-X-Y's may be the same as or different from each other. When a repetition of a sequence represented by Gly-X-Y is provided, there are few restrictions on the arrangement of molecular chains, and a function as a scaffolding material becomes better. In the extracellular matrix components having a repetition of a sequence represented by Gly-X-Y, the proportion of the sequence represented by Gly-X-Y among all amino acid sequences may be 80% or more and is preferably 95% or more. In addition, the extracellular matrix components may have an RGD sequence. The RGD sequence is a sequence represented by Arg-Gly-Asp (arginine residue-glycine residue-aspartic acid residue). When the extracellular matrix components have an RGD sequence, cell adhesion is further promoted, and the component becomes more suitable as a scaffolding material. The extracellular matrix components including the sequence represented by Gly-X-Y and the RGD sequence include collagen, fibronectin, vitronectin, laminin, cadherin and the like.

The concentration of the extracellular matrix component when it is brought into contact with cells in the aqueous medium based on the total amount of the aqueous medium may be 0.001 mg/mL or more, 0.01 mg/mL or more, 0.025 mg/mL or more, 0.05 mg/mL or more, 0.1 mg/mL or more, 0.2 mg/mL or more, 0.3 mg/mL or more, 0.4 mg/mL or more, or 0.5 mg/mL or more. The concentration of the extracellular matrix component when it is brought into contact with cells in the aqueous medium based on the total amount of the aqueous medium may be, for example, 10.0 mg/mL or less, 8.0 mg/mL or less, 6.0 mg/mL or less, 5.0 mg/mL or less, 3.0 mg/mL or less, 1.0 mg/mL or less, 0.8 mg/mL or less, or 0.6 mg/mL or less. The concentration of the extracellular matrix component when it is brought into contact with cells in the aqueous medium based on the total amount of the aqueous medium may be 0.001 mg/mL or more and 10.0 mg/mL or less, 0.01 mg/mL or more and 6.0 mg/mL or less, 0.025 mg/mL or more and 5.0 mg/mL or less, 0.05 mg/mL or more and 1.0 mg/mL or less, 0.1 mg/ml or more and 0.8 mg/mL or less, or 0.2 mg/mL or more and 0.6 mg/ml or less.

The amount of the extracellular matrix component in the contact step may be 0.001 mg or more or 0.01 mg or more, and may be 1 mg or less or 0.1 mg or less with respect to 300,000 cells (the number of cells when they are brought into contact with the extracellular matrix component).

The order in which the cells are brought into contact with the above components is not particularly limited, and for example, some cells may be brought into contact with the above components, the remaining cells may be then brought into contact with the above components, or all cells may be brought into contact with the above components simultaneously or substantially simultaneously.

The aqueous medium may or may not be mixed by stirring or the like after the above components are added. The contact step may include incubating for a certain time after the cells are brought into contact with the above components. Examples of the certain time include 1 minute, 3 minutes, 5 minutes, 10 minutes, 15 minutes, 30 minutes, 1 hour, 2 hours, and 3 hours. The incubation time may be, for example, 1 minute or longer and 3 hours or shorter, or 1 minute or longer and 15 minutes or shorter.

Incorporation of fibrinogen and thrombin may be provided in the contact step or after the contact step and before the culture step. For example, fibrinogen and thrombin may be added at the same time, or one may be added first and then the other may be added. In the contact step, for example, a solution containing fibrinogen and a solution containing thrombin may be mixed simultaneously or separately with a cell component containing cells and heparin. For example, when equal amounts or substantially equal amounts of a thrombin solution with a concentration of 20 U/mL and a fibrinogen solution with a concentration of 10 mg/mL are used, fibrinogen and thrombin may be incorporated.

When fibrinogen and thrombin are added, shrinkage that may occur in the culture step to be described below is more likely to be minimized, and the shape and size of the cell aggregate can be easily controlled. In addition, since a cell suspension can be gelled, the state in which the cells and the above components are uniformly mixed is maintained, and the state in which the cells are brought close to the above components is easily maintained. In the contact step or after the contact step and before the culture step, when fibrinogen and thrombin are incorporated, cell dispersion in the medium during cell seeding is further minimized and it is possible to form cell aggregates with a smaller amount of cells.

The method may include, after the cells are brought into contact with the above components, accumulating the cells and the above components (heparin and/or extracellular matrix components) to remove aqueous components, and adding an aqueous medium to aggregates of the cells and the above components obtained by accumulating to obtain a cell suspension again. The cell suspension thus obtained may be subjected to the culture step to be described below. As an accumulating method, a method of centrifuging the entire aqueous medium may be exemplified. Aggregates of cells and the above components may be, for example, viscous components. As an aqueous medium for resuspension, a culture medium may be exemplified. When aggregates of cells and the above components are formed, the cells can be surrounded by the above components (that is, buried), and when aggregates of cells and the above components are re-suspended in the medium, the process can proceed to the culture step while they are buried to some extent. When aggregates of cells and the above components are re-suspended, the viscosity is sufficiently low, and it becomes easier to handle them with a pipette or the like.

In the culture step, the cells in contact with heparin are cultured to form a cell aggregate having bile canaliculi. Cell culture is performed under conditions in which cells can grow. When cells in contact with extracellular matrix components in addition to heparin are cultured, it is possible to form a cell aggregate in which extracellular matrix components are disposed between at least some cells in the cell aggregate.

The medium used in the culture step may not contain insulin and transferrin, which are proteins secreted from the liver. Examples of mediums used in the culture step include a medium for vascular endothelia (for example, EGM2 (commercially available from Lonza), EGM2-MV (commercially available from Lonza), Endothelial Cell Growth Medium 2 (commercially available from Promocell), Endothelial Cell Growth Medium MV 2 (commercially available from Promocell), and ECM (commercially available from ScienceII). The medium may be a medium to which serum is added or a serum-free medium. The medium may be a mixed medium in which two types of mediums are mixed. For example, a mixed medium in which a medium for vascular endothelia and a medium for mesenchymal stem cell proliferation are mixed may be used.

The culture temperature in the culture step may be, for example, 20° ° C. to 40° C. or 30° ° C. to 37° C. The pH of the medium may be 6 to 8 or 7.2 to 7.4. The culture time may be 1 day or longer, 1 day to 2 weeks, or 1 week to 2 weeks.

The culture container (support) is not particularly limited, and may be, for example, a dish, a well insert, a low adhesive plate, or a plate having a bottom shape such as a U shape and a V shape. The cells may be cultured while adhered to the support or the cells may be cultured without being adhered to the support or may be separated from the support during culture and cultured. When the cells are cultured without being adhered to the support or are separated from the support during culturing and cultured, it is preferable to use a plate having a bottom shape such as a U shape and a V shape that inhibits adhesion of the cells to the support or a low adsorption plate.

The cell density in the medium in the culture step can be appropriately determined according to the shape and thickness of a desired cell aggregate, the size of the culture container and the like. For example, the cell density in the medium in the culture step may be 1 to $10^8$ cells/mL or $10^3$ to $10^7$ cells/mL. In addition, the cell density in the medium in the culture step may be the same as the cell density in the aqueous medium in the contact step.

After the culture step (hereinafter referred to as a "first culture step", and an initial contact step is referred to as a "first contact step"), additionally, a step of contacting cells (second contact step), and a step of culturing the cells (second culture step) may be provided. The cells in the second contact step and the second culture step may be the same species as or a different species from the cells used in the first contact step and the first culture step. According to the second contact step and the second culture step, it is possible to produce a cell aggregate having a two-layer structure. In addition, when the contact step and the culture step are repeatedly included, it is possible to produce a cell aggregate having a plurality of layers and it is possible to produce a tissue that is closer to a more complex living body.

The cell aggregate according to the present embodiment has bile canaliculi. Bile canaliculi are spaces located between cells including hepatocytes, particularly, spaces located between contacting hepatocytes. In vivo, bile acids taken up by hepatocytes are known to be excreted into bile canaliculi. The fact that the cell aggregate has bile canaliculi can be confirmed, for example, by expression of multidrug resistance-associated protein 2 (MRP2), which is a transporter on bile canaliculi. The expression of MRP2 can be confirmed by the method described in examples to be described below. In addition, the fact that the cell aggregate has bile canaliculi can be confirmed, for example, by bringing optically detectable labeled bile acids into contact with the cell aggregate and detecting the bile acids retained in the cells and in the bile canaliculi. Retention of bile acids in cells or bile canaliculi can be confirmed by the method described in examples to be described below.

In the cell aggregate according to the present embodiment, the expression intensity percentage of MRP2 represented by the following Formula (1) may be more than 100%.

$$\text{expression intensity percentage of MRP2}=X/Y\times 100 \quad (1)$$

In Formula (1), X indicates an expression intensity of MRP2 in the cell aggregate formed in the culture step, and Y indicates an expression intensity of a control cell aggregate formed by culturing cells including hepatocytes without contact with heparin and extracellular matrix components. In the contact step, when cells are not brought into contact with extracellular matrix component, the control cell aggregate is a cell aggregate produced under the same conditions as the cell aggregate (test cell aggregate) formed in the above culture step except that cells are not brought into contact with heparin. In the contact step, when cells are brought into contact with extracellular matrix components, the control cell aggregate is a cell aggregate produced under the same conditions as the test cell aggregate except that cells are not brought into contact with heparin and cells are not brought into contact with extracellular matrix components. Specific conditions may be those described in examples to be described below. The culture period of the test cell aggregate and the control cell aggregate may be 1 day or longer or 3 days or longer or may be 3 days.

The expression intensity percentage of MRP2 in the cell aggregate according to the present embodiment may be 105% or more, 110% or more, 120% or more, 130% or more, 140% or more, 150% or more, 160% or more, 170% or more, or 180% or more. The expression intensity percentage of MRP2 in the cell aggregate according to the present embodiment may be, for example, 300% or less, or 250% or less.

The cell aggregate according to the present embodiment can be suitably used as a hepatotoxicity evaluation model for drugs, tissues for transplantation into non-human animals, and the like.

EXAMPLES

Hereinafter, the present invention will be described in detail with reference to examples. However, the present invention is not limited to these examples.

1. Experiment Procedure

[Material, Instrument and Device Used]

The following cultured cells, materials, instruments and devices were prepared.

(Cultured Cells)

TABLE 1

| Cell line | Origin/tissue | Manufacturer | Model number | Culture medium |
|---|---|---|---|---|
| Lx2 | Human hepatic stellate cells | MerckMilliporer | SCC064 | D-MEM (with 2% (v/v) FBS, 1% (v/v) P/S) |
| SEC | Human liver sinusoidal endothelial cells | SCIENCELL | 5000 | ECM |
| PXBcell | Human hepatocyte chimeric mouse-derived fresh human hepatocytes | PhoenixBio | PPC-T25 | HCGM |

(Reagents and Consumables)

TABLE 2

| Type | Name | Manufacturer | Note |
|---|---|---|---|
| Medium | DMEM | Nacalai Tesque | high glucose |
| Medium | ECM | Sciencell | |
| Medium | HCGM | PhoenixBio | |
| Medium | HCM | Lonza | |
| Reagent | FBS: Fetal bovine serum | Thermo Fisher | |
| Reagent | p/s: penicillin-streptomycin solution | FUJIFILM Wako Pure Chemical Corporation | |
| Reagent | heparin (hydrochloride) | Sigma-Aldrich | derived from porcine intestinal mucosa |
| Reagent | collagen | Nippi | Type I, derived from bovine dermis |
| Reagent | acetic acid | FUJIFILM Wako Pure Chemical Corporation | |
| Reagent | Tris (hydrochloride) | Sigma-Aldrich | |
| Reagent | PBS: phosphate buffer solution | Nacalai Tesque | |
| Reagent | TBS containing 0.05% Triton | Nacalai Tesque | |
| Reagent | 0.25% trypsin-EDTA | FUJIFILM Wako Pure Chemical Corporation | |
| Reagent | Trypan blue | Invitrogen | |
| Reagent | 4% paraformaldehyde/•phosphate buffer solution | FUJIFILM Wako Pure Chemical Corporation | |
| Reagent | TRITON X-100 | MP Biomedicals | |
| Reagent | BSA: bovine serum albumin | Thermo Fisher | |
| Reagent | Thrombin from bovine plasma | SIGMA | |

TABLE 2-continued

| Type | Name | Manufacturer | Note |
|---|---|---|---|
| Reagent | Live/Dead Cell Staining Kit II | PROMOCELL | |
| Reagent | Endothelial Cells Growth Supplement | Sciencell | |
| Antibody | Mouse-derived anti-CD31 antibody | DAKO | clone: M0823 |
| Antibody | Mouse-derived anti-MRP-2 antibody | TAKARA BIO | clone: M-III |
| Antibody | Mouse-derived anti-E-cadherin antibody | abcam | clone: HECD-1 |
| Antibody | Alexa647-labeled anti mouse IgG secondary antibody | Thermo Fisher | host: goat |
| Instrument | 48-well plate | IWAKI | |
| Instrument | 96-well microplate | IWAKI | |

(1) Cell Counting Device
Invitrogen Countess (registered trademark) II FL
(2) Microscope
Confocal microscope CQ1 (commercially available from Yokogawa Electric Corporation)
(3) Others
Image analysis software: Image J (Fiji) individual installation plugin:
Mexican Hat Filter Test Example 1: Confirmation of Aggregation Behavior of Cells Treated with Heparin/Collagen It was verified what kinds of aggregation behavior cells exhibited when cells were treated with either or both of heparin and collagen.
[Treatment of Cells with Heparin/Collagen]
PXB cells, SEC and LX2 were used as cells.
Step 1-1
(Collection of cells other than PXB cells) The frozen stock of each cell of Lx2 and SEC was cultivated and cultured without subculture intervening based on the protocol recommended by the manufacturer, cells were collected from a culture flask and a petri dish using trypsin based on a general method, and the amount of each cell was the measured.
Step 1-2
(Collection of PXB cells) Collection was performed according to the following procedure and the amount of cells was measured.
PXB cells were washed with PBS. 0.25% trypsin-EDTA was added to the washed PXB cells, incubated in an incubator, and the PXB cells were then collected. The amount of the collected PXB cells was measured with a cell counter.
Step 1-3
The collected cells were mixed at the following ratios and cell amounts to obtain a cell mixture.
total amount of cells: 300,000 cells
cell proportions in tissue:
PXB cells: 65%·SEC: 25%·LX2: 10%
Step 1-4
100 μL of each of the following solutions was added to the cell mixture at room temperature, suspended until the cells were no longer visible, and then centrifuged (400 g×2 min) to obtain a viscous component. Here, regardless of the presence of heparin and collagen, it was confirmed in advance that the pH of each solution was approximately around 7.4.
(1) 100 mM Tris-HCl buffer solution
(2) collagen-containing solution (0.2 mg/mL collagen in 100 mM Tris-HCl buffer solution*)
(3) collagen and heparin-containing solution (0.2 mg/mL collagen and 0.5 mg/mL heparin in 100 mM Tris-HCl buffer solution)
*Since collagen quickly gelled in a neutral solution at room temperature, equal amounts of a 0.4 mg/mL collagen in 5 mM acetate buffer solution and a 200 mM Tris-HCl buffer solution prepared in advance were mixed in each of the above solutions and used.
Step 1-5
After the supernatant was removed from the solution containing the viscous component, HCM was added so that the final volume of the solution was a solution amount of 100 μL to obtain a cell suspension.
Step 1-6
The cell suspension was seeded at 10 μL/well in a 96-well microplate in which 190 μL of HCM was added to each well in advance, and suspended in the wells.
[Observation of Live Cells Under Confocal Microscope]
A 96-well microplate in which the cell suspension was seeded and suspended was set in a confocal microscope in which the temperature inside the device was set to 37° C. in advance and 5% $CO_2$ was supplied, and the aggregation state over time was observed from 30 minutes to 6 hours after seeding.

Test Example 2: Formation of Tissue of Cells Treated with Heparin/Collagen in Fibrin Gel Regarding hepatotoxicity models treated with each solution, it was evaluated whether there was a difference in the state of adhesion between hepatocytes.
[Construction and Culture of Hepatotoxicity Model]
Step 2-1
A cell mixture with the following proportions and cell amounts was obtained in the same procedures as Steps 1-1 to 1-3 in Test Example 1.
total amount of cells: 300,000 cells
cell proportions in tissue:
PXB cell: 65%·SEC: 25%·LX2: 10%
Step 2-2
100 μL of each of the following solutions was added to the cell mixture at room temperature, suspended until the cells were no longer visible, and then centrifuged (400 g×2 min) to obtain a viscous component. Here, regardless of the presence of heparin/collagen, it was confirmed in advance that the pH of each solution was approximately around 7.4.
(1) 100 mM Tris-HCl buffer solution
(2) collagen-containing solution (0.2 mg/mL collagen in 100 mM Tris-HCl buffer solution*)

(3) heparin-containing solution (0.5 mg/mL heparin in 100 mM Tris-HCl buffer solution)

(4) collagen- and heparin-containing solution (0.2 mg/mL collagen and 0.5 mg/mL heparin in 100 mM Tris-HCl buffer solution)

Since collagen quickly gelled in a neutral solution at room temperature, equal amounts of a 0.4 mg/mL collagen in 5 mM acetate buffer solution and a 200 mM Tris-HCl buffer solution prepared in advance were mixed in each of the above solutions and used.

Step 2-3

After the supernatant was removed from the solution containing the viscous component obtained in Step 2-2, a 20 U/mL thrombin solution (solvent: HCM) was added so that the final volume of the solution was a solution amount of "the number of wells to be seeded"×2 μL to obtain a cell suspension.

Step 2-4

2 μL of a 10 mg/mL fibrinogen solution was seeded on a 48-well microplate to form droplets and each cell suspension obtained in Step 2-3 was then added into the droplets, and then left in an incubator for 1 hour to form a fibrin gel.

Step 2-5

0.5 mL of HCM (containing Endothelial Cell Growth Supplement) was added to each well in which the fibrin gel was formed.

Step 2-6

After HCM was added, culture was continued for 3 days in each well in which the fibrin gel was formed.

[Fixation, Immunostaining and Microscope Imaging of Hepatotoxicity Model]

After the live cells were observed in the same method as in Test Example 1, culture was continued for 3 days of culture, and hepatotoxicity model evaluation was performed for each sample, as described below, by a method including a fixation treatment, a transmission treatment, blocking, a primary antibody treatment, a secondary antibody treatment, imaging/area calculation and evaluation in that order.

(Fixation Treatment)

After 3 days of culture, the 48-well microplate was removed from the incubator, the medium was removed, washing with PBS was performed, and 300 μL of a 4% paraformaldehyde·phosphate buffer solution (hereinafter referred to as PFA) was then added to each well to fix a hepatotoxicity model (3D model). Then, the PFA was washed thoroughly and removed.

(Transmission Treatment/Blocking)

100 μL of a 0.2 (v/v) % TRITON/1 (w/v) % BSA PBS solution (hereinafter referred to as a BSA solution) was added to each well, and left at room temperature for 2 hours.

(Primary Antibody Treatment)

Anti-MRP2 antibodies were diluted 100-fold with a BSA solution to obtain a primary antibody solution. 100 μL of the primary antibody solution was added to each well and left at 4° C. for 24 hours. Then, the primary antibody solution was washed thoroughly and removed.

(Secondary Antibody Treatment)

Secondary antibodies were diluted 200-fold with a BSA solution to obtain a secondary antibody solution. 100 μL of the secondary antibody solution was added to each well, shielded from light and left at room temperature for 1 hour. Then, the secondary antibody solution was washed thoroughly and removed, and 100 μL of PBS was added to each well.

(Fluorescence Microscope Imaging)

Images were captured under a confocal microscope. Imaging conditions were as follows.

lens used: 10× lens
imaging mode: confocal
filter: 647 (Ex)/678 (Em)
Z-axis position: 0-100 μm/5 μm increments The intensities of the captured images were summed to obtain a fluorescence observation image of each hepatotoxicity model (3D model).

[Image Analysis of Observation Image (MRP2)]

A 1.2 $mm^2$ area in the approximate center of the observed MRP2 immunostained image of each hepatotoxicity model was cut out and subjected to image analysis using ImageJ as described below.

(1) Image>Type>8-bit (2) Process>Subtract Background>Sliding Paraboloid (20 pixels)

(3) Image>Adjust>Threshold (range: 25-255)

(4) Analyze>Set measurements>area (5) Analyze>tools>ROI manager
Select all
add
measure Test Example 3: Confirmation of Formation of Bile Canaliculi According to Bile Acid Assay A hepatotoxicity model was produced according to the same method as in the method described in Test Examples 1 and 2. However, the collagen concentration was 0.3 mg/mL, and the heparin concentration was 0.05 mg/mL, 0.15 mg/mL, 0.5 mg/mL, or 5.0 mg/mL (all final concentrations).

After 6 days of culture, the medium was replaced with 300 μL of a medium containing 5 μM CLF (FITC-labeled bile acid CORNING #451041) on which the following operation was performed (this assay was performed while cells were alive). After being left in the incubator for 20 min, the tissue was washed with PBS 5 times. The medium was replaced, and observation was performed under a fluorescence microscope.

2. Experiment Results and Consideration

Test Example 1: Confirmation of Aggregation Behavior of Cells Treated with Heparin/Collagen FIG. 1 shows fluorescence images obtained when cells were treated with FITC-modified collagen or heparin in advance, and the state of deposition of these molecules on the cells was confirmed. In FIG. 1, the scale bar indicates 100 μm.

A difference in tendencies in which relatively more collagen was deposited on the surface of the cells while heparin was deposited inside the cells was observed, but deposition of molecules according to the treatment was confirmed.

Here, although not shown, when collagen and heparin not labeled with FITC were used, almost no fluorescence was observed with the same contrast, and it was confirmed that the fluorescence in FIG. 1 was derived from FITC.

In Test Example 1, the cells treated with each solution were seeded in a 96-well microplate and live cells were observed up to 6 hours after seeding, and the results are shown in FIG. 2.

Based on the results in FIG. 2, it was confirmed that, when cells were treated with a solution containing collagen (solution (2) in Test Example 1) and a solution containing heparin together with collagen (solution (3) in Test Example 1), at the stage 2 hours after seeding, for example, aggregation of cells was significantly promoted in areas indicated by broken-line frames in FIG. 2.

When a neutral solution containing collagen alone was prepared, it quickly gelled at room temperature and it was difficult to handle as a liquid. In this experiment, a Tris-HCl buffer solution was added to the acetate solution containing collagen immediately before use to adjust the pH to 7.4 and thus it was barely treated as a solution, but it was thought that gelation at the microlevel was progressing inside and the state was not completely stable, and thus there was a concern that this method could cause errors in each experiment. If heparin was added in advance, the solution did not gel at room temperature for a long time, the solution was stabilized, and thus the experiment could be performed stably.

Based on the above results, a cell aggregation promoting effect according to a heparin/collagen treatment was confirmed.

Test Example 2: Formation of Tissue of Cells Treated with Heparin/Collagen in Fibrin Gel FIG. 3 shows the results of staining with MRP2 for the hepatotoxicity model produced under respective conditions. In FIG. 3, the scale bar in images of Bright Field and Fluorescence indicates 500 μm, and the scale bar in the enlarged view indicates 300 μm.

According to the results of FIG. 3, under treatment conditions in which collagen alone was contained, cells tended to aggregate excessively, and as a result, the expression of MRP2 tended to decrease significantly. Although the difference between other conditions was not very significant, under heparin-treated conditions, and heparin/collagen-treated conditions, a state in which the fluorescence was enhanced as a whole compared to control conditions was found.

Therefore, the center part of the image was cut out, the area of a signal range exceeding the background level was calculated by image analysis, and respective conditions were compared.

Figure 4:
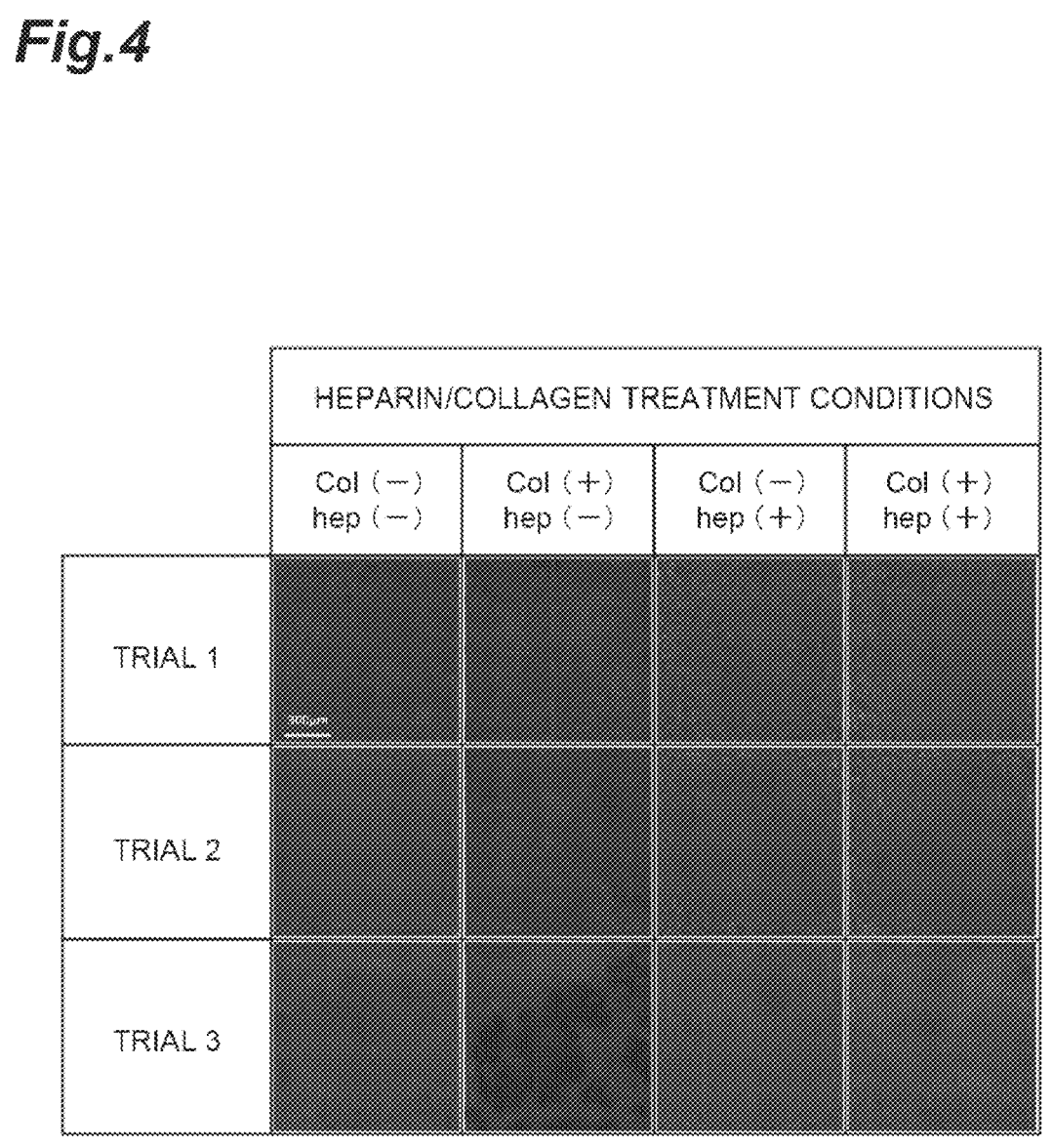

FIG. 4 shows images of the fluorescence observation results of the MRP2 expression under various treatment conditions. In FIG. 4, the scale bar indicates 300 μm. FIG. 5 is a graph showing the expression intensity percentage (expression area percentage) per area calculated based on the image analysis of the hepatotoxicity model shown in FIG. 4.

FIG. 5 shows the results quantitatively supporting the claim that the hepatotoxicity models obtained through a heparin treatment and a heparin/collagen treatment had a higher expression intensity percentage of MRP2 than the control.

Figure 6:
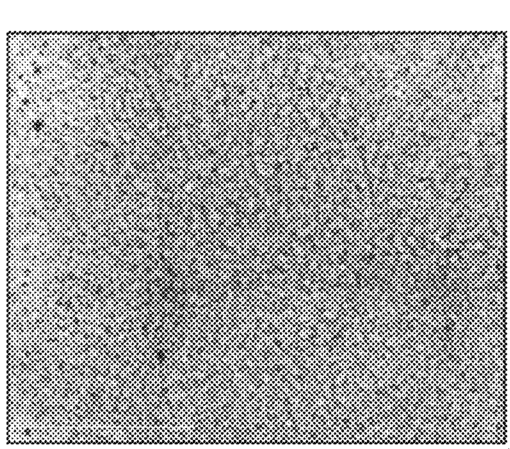
FIG. 6 shows microscope images of the bile acid assay results, FIG. 6(*a*) shows a bright field, FIG. 6(*b*) shows fluorescence, and FIG. 6(*c*) is an image of (a) and (b) merged.
Figure 6:
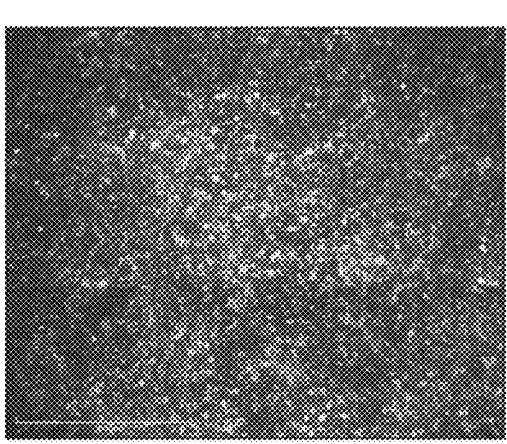
Figure 6:
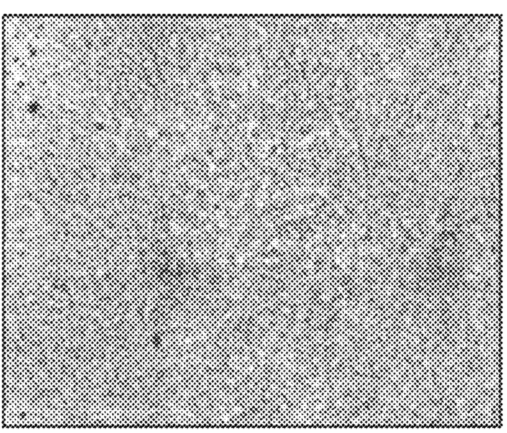

Test Example 3: Confirmation of Formation of Bile Canaliculi According to Bile Acid Assay FIG. 6, FIG. 7, FIG. 8, and FIG. 9 show the results of fluorescence observation after a medium containing CLF was incubated for the hepatotoxicity models produced with different heparin concentrations. FIG. 6 shows the results of fluorescence observation of the control hepatotoxicity model. In each drawing, the scale bar indicates 500 μm. In normal live tissue in which bile canaliculi were favorably formed, it was thought that, since hepatocytes excreted bile acids taken up from the outside of the live tissue into the bile canaliculi, the intensity of fluorescence derived from FITC retained in the cells was low after the CLF treatment.

Figure 7:
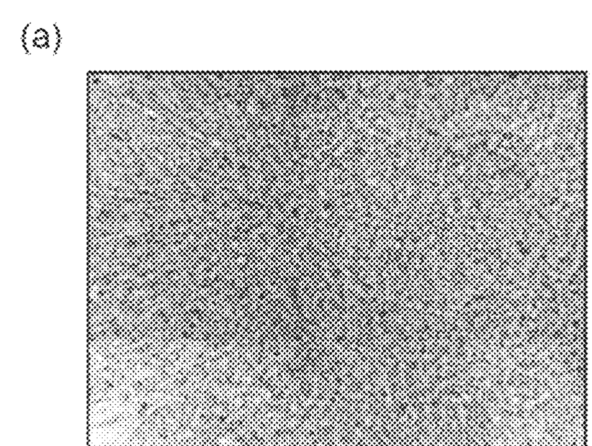
FIG. 7 shows microscope images of the bile acid assay results, FIG. 7(*a*) shows a bright field, FIG. 7(*b*) shows fluorescence, and FIG. 7(*c*) is an image of (a) and (b) merged.
Figure 7:
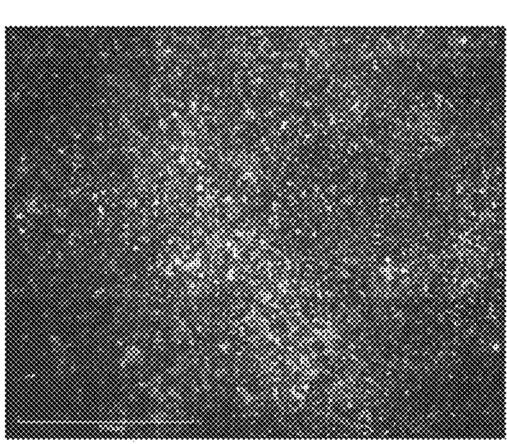
Figure 7:
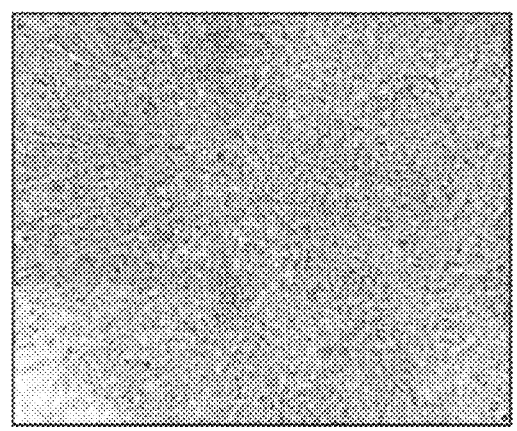
Figure 8:
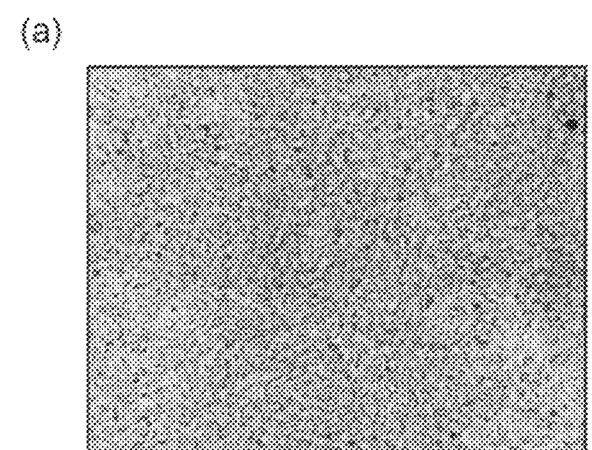
FIG. 8 shows microscope images of the bile acid assay results, FIG. 8(*a*) shows a bright field, FIG. 8(*b*) shows fluorescence, and FIG. 8(*c*) is an image of (a) and (b) merged.
Figure 8:
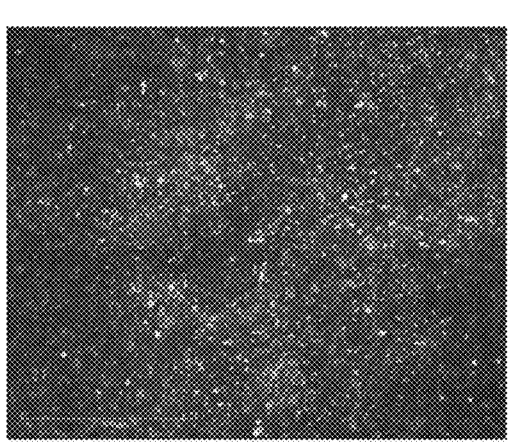
Figure 8:
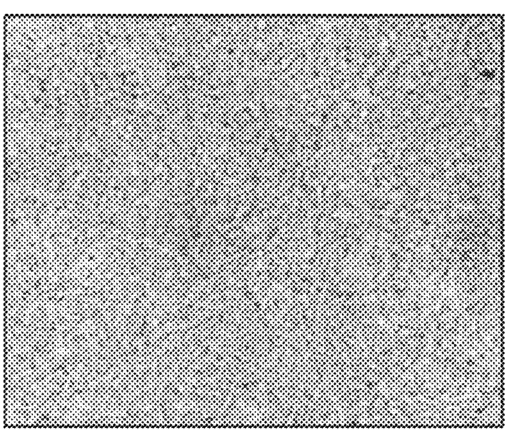

In FIG. 7, FIG. 8, and FIG. 9 in which the heparin concentration when the hepatotoxicity model was produced was 0.15 mg/mL, 0.5 mg/mL, or 5.0 mg/mL, it was confirmed that, although the intensity of fluorescence derived from FITC in the cells was low, a large intensity of fluorescence derived from FITC was observed outside the cells, CLF taken into hepatocytes was more efficiently excreted into the bile canaliculi, and thus retention in the hepatocytes was further inhibited. In addition, it was observed that, if the heparin concentration when the hepatotoxicity model was produced increased, the intensity of fluorescence derived from FITC retained in the cells decreased and the intensity of punctate or linear fluorescence around cells increased.

That is, it was confirmed that, if heparin was used when the hepatotoxicity model was produced, CLF taken into hepatocytes was easily excreted into the bile canaliculi.

The invention claimed is:

1. A method for producing a cell aggregate comprising bile canaliculi, comprising:

a contact step of bringing cells comprising hepatocytes into contact with heparin in an aqueous medium; and a culture step of culturing the cells brought in contact with the heparin to form the cell aggregate, wherein a concentration of heparin in the aqueous medium when brought into contact with the cells is 0.5 mg/mL or more.

2. The method according to claim 1, wherein the hepatocytes are mature hepatocytes.

3. The method according to claim 1, wherein the proportion of the number of hepatocytes in the total number of cells is 65% or more.

4. The method according to claim 1, wherein, in the contact step, the cells are additionally brought into contact with extracellular matrix components.

5. The method according to claim 4, wherein the extracellular matrix components are collagen components.

6. The method according to claim 1, wherein the expression intensity percentage of multidrug resistance-associated protein 2 (MRP2) in the cell aggregate represented by the following Formula (1) is 120% or more, $$\text{expression intensity percentage of MRP2} = X/Y \times 100 \quad (1)$$

wherein in Formula (1),

X represents an expression intensity of MRP2 in the cell aggregate formed in the culture step, and Y represents an expression intensity of a control cell aggregate formed by culturing cells comprising hepatocytes without contact with heparin and extracellular matrix components.

7. The method according to claim 1, wherein the concentration of heparin in the aqueous medium when brought into contact with the cells is 0.5 mg/mL or more and 12.0 mg/mL or less.

8. The method according to claim 1, wherein the concentration of heparin in the aqueous medium when brought into contact with the cells is 0.5 mg/mL or more and 5.0 mg/mL or less.

* * * * *